(12) United States Patent
Togashi et al.

(10) Patent No.: US 8,118,167 B2
(45) Date of Patent: Feb. 21, 2012

(54) MEDICAL CONTAINER

(75) Inventors: Hiroshi Togashi, Tochigi (JP); Scott Young, Kennett Square, PA (US); Edward F. Vander Bush, Jr., Downingtown, PA (US)

(73) Assignees: Daikyo Seiko, Ltd., Tokyo (JP); West Pharmaceutical Services, Inc., Lionville, PA (US)

( * ) Notice: Subject to any disclaimer, the term of this patent is extended or adjusted under 35 U.S.C. 154(b) by 0 days.

(21) Appl. No.: 12/526,819

(22) PCT Filed: Mar. 5, 2007

(86) PCT No.: PCT/JP2007/054188
§ 371 (c)(1),
(2), (4) Date: Aug. 12, 2009

(87) PCT Pub. No.: WO2008/107961
PCT Pub. Date: Sep. 12, 2008

(65) Prior Publication Data
US 2010/0012546 A1    Jan. 21, 2010

(51) Int. Cl.
*B65D 83/04* (2006.01)
*B65D 85/42* (2006.01)

(52) U.S. Cl. ...................... 206/534.1; 206/519

(58) Field of Classification Search .............. 206/534.1, 206/535, 372, 373, 518–520, 515; 53/434, 53/474; 220/651, 529, 553, 554; 211/126.1, 211/85.18, 85.13; 34/285; 422/266, 270, 422/300
See application file for complete search history.

(56) References Cited

U.S. PATENT DOCUMENTS

| | | | |
|---|---|---|---|
| 5,176,284 A * | 1/1993 | Sorensen | 220/659 |
| 5,887,715 A * | 3/1999 | Vasudeva | 206/373 |
| 6,907,679 B2 * | 6/2005 | Yarborough et al. | 34/285 |

(Continued)

FOREIGN PATENT DOCUMENTS

| | | |
|---|---|---|
| JP | 62-266061 A | 11/1987 |
| JP | 07-300188 A | 11/1995 |
| JP | 11-314692 A | 11/1999 |
| JP | 2004-513707 A | 5/2004 |
| JP | 2004-513708 A | 5/2004 |

(Continued)

OTHER PUBLICATIONS

International Search Report for PCT/JP2007/054188 dated on Mar. 27, 2007.

*Primary Examiner* — Mickey Yu
*Assistant Examiner* — Rafael Ortiz
(74) *Attorney, Agent, or Firm* — Kenealy Vaidya LLP (57) ABSTRACT

The present invention relates to a medical container useful upon transportation of plural syringe barrels. The medical container includes at least a container main body and a holding member arranged inside the container main body. The holding member is provided at least with a plurality of cylindrical holding portions for holding syringe barrels. The container main body has at least a peripheral rim arranged on and along an outer periphery of an opening and a shoulder-shaped portion arranged on an inner wall of the container to arrange the holding member. The shoulder-shaped portion has at least three ribs for supporting the holding member, and has a structure that enables to arrange via the ribs the holding member in a horizontal position relative to a bottom wall of the container main body. According to the present invention, there is provided a medical container of a construction that can be promptly brought into a sterilized state by various methods, can be readily brought into a state capable of maintaining the sterilized state, and during transportation, can fixedly secure, without rattling, syringe barrels held upright by holders.

6 Claims, 7 Drawing Sheets

U.S. PATENT DOCUMENTS

| | | | |
|---|---|---|---|
| 7,017,740 B2 * | 3/2006 | Itzkovitch | 206/372 |
| 7,232,038 B2 * | 6/2007 | Whitney | 211/74 |
| 2004/0134818 A1 * | 7/2004 | Cunningham et al. | 206/373 |
| 2006/0016156 A1 * | 1/2006 | Bush et al. | 53/434 |
| 2006/0060588 A1 * | 3/2006 | Tonelli | 220/554 |

FOREIGN PATENT DOCUMENTS

| | | |
|---|---|---|
| JP | 2005-178815 A | 7/2005 |
| JP | 2005-529803 A | 10/2005 |
| JP | 2006-513782 A | 4/2006 |

* cited by examiner

MEDICAL CONTAINER

This application is a U.S. national phase filing under 35 U.S.C. §371 of PCT
Application No. PCT/JP2007/054188, filed Mar. 5, 2007.

TECHNICAL FIELD

This invention relates to a medical container capable of storing and transporting a plurality of syringe barrels.

BACKGROUND ART

Figure 6:
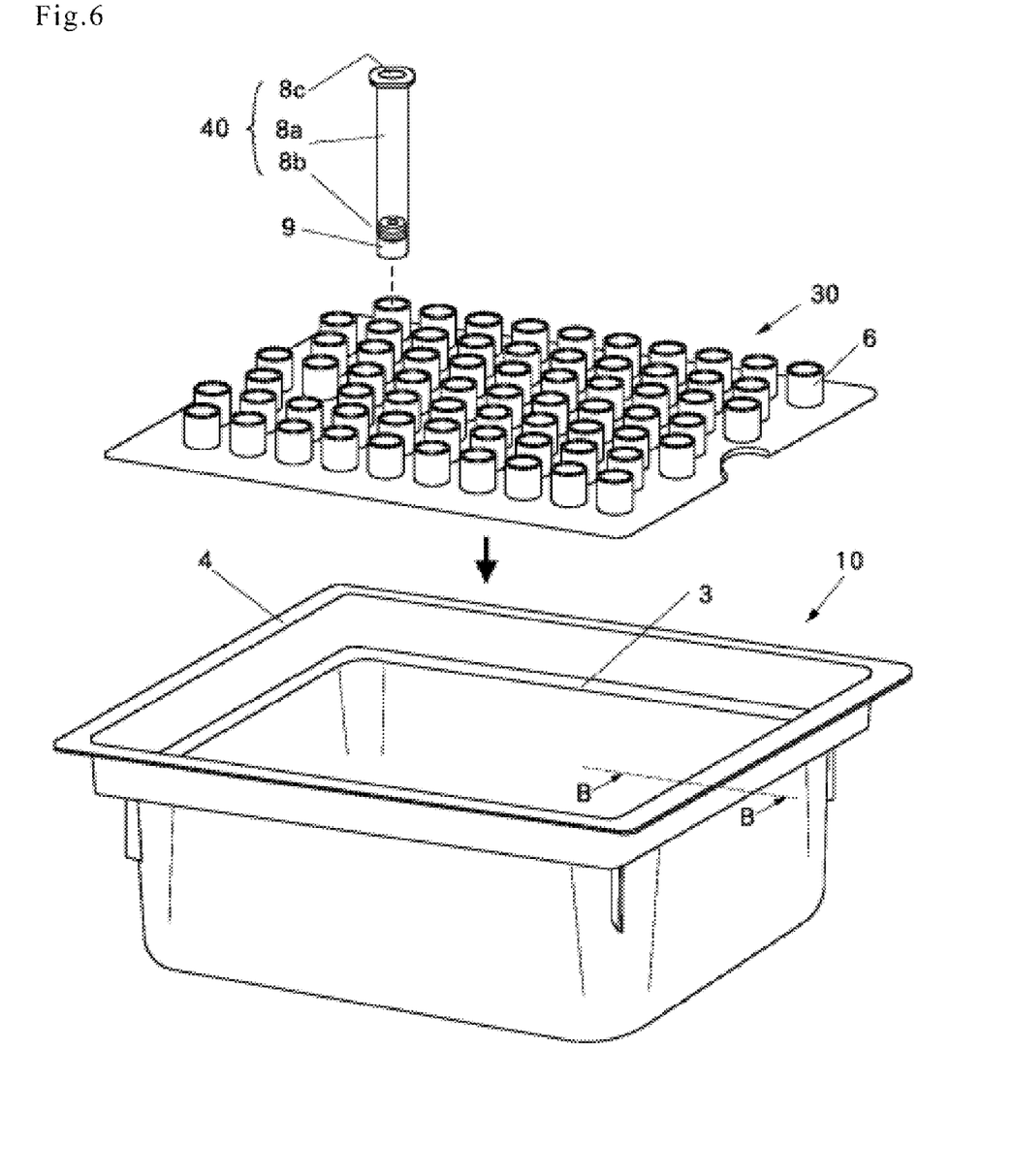
FIG. 6 A perspective view for describing the construction of one example of conventional medical containers.

For the transportation and storage of syringe barrels before their filling with a medicament or the like, there have been widely employed for years medical containers each of which can hold plural syringe barrels together in an upright position. As illustrated in FIG. 6, such a container 10 is generally in the form of an upwardly open box, and has a structure that a shoulder-shaped portion 3 is arranged on an upper part of its inner wall and a holder 30 capable of holding plural syringe barrels in an upright position is arranged as a nest inside the container 10. The holder 30 (nest) is of a construction that plural cylinders (holding portions) 6 having through-holes therein are arranged upright on a plate-shaped member and the syringe barrels can be held in position by inserting syringe barrels 40 from one sides 8b, at which syringe needles are to be fitted, and hooking flange portions of the syringe barrels on upper ends of the cylinders 6.

Figure 3:
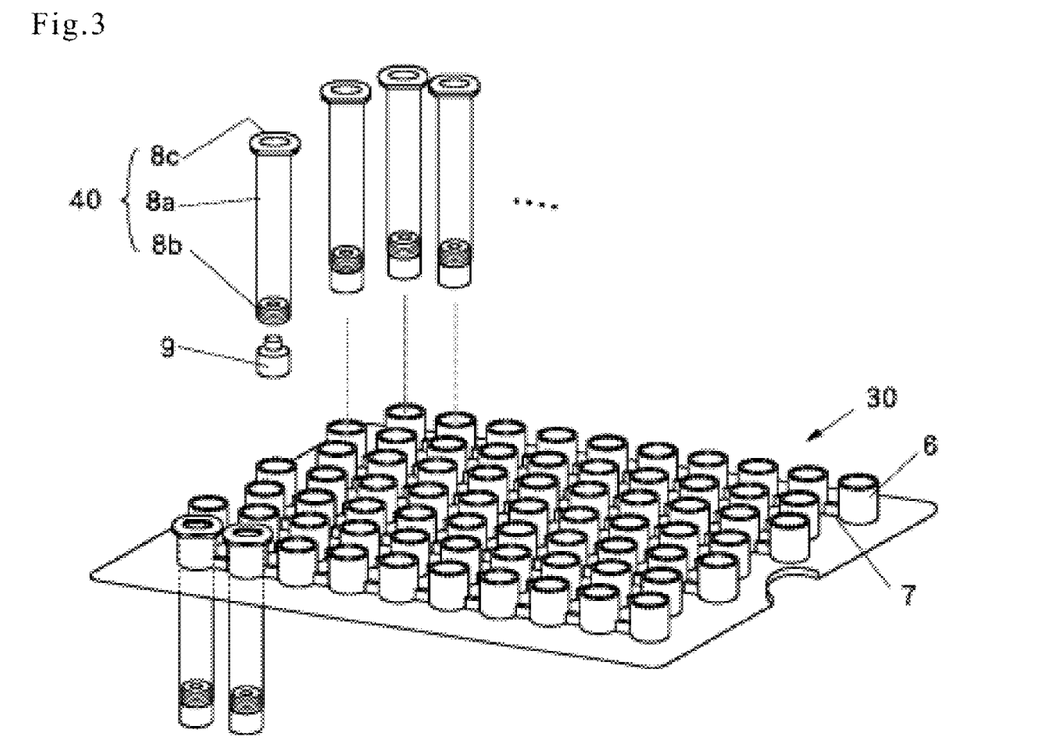
FIG. 3 A perspective view for describing a state that a syringe barrel 40 with a nozzle cap 9 applied to a tip thereof is to be held on the holder 30 constituting the medical container according to the present invention.
Figure 7A:
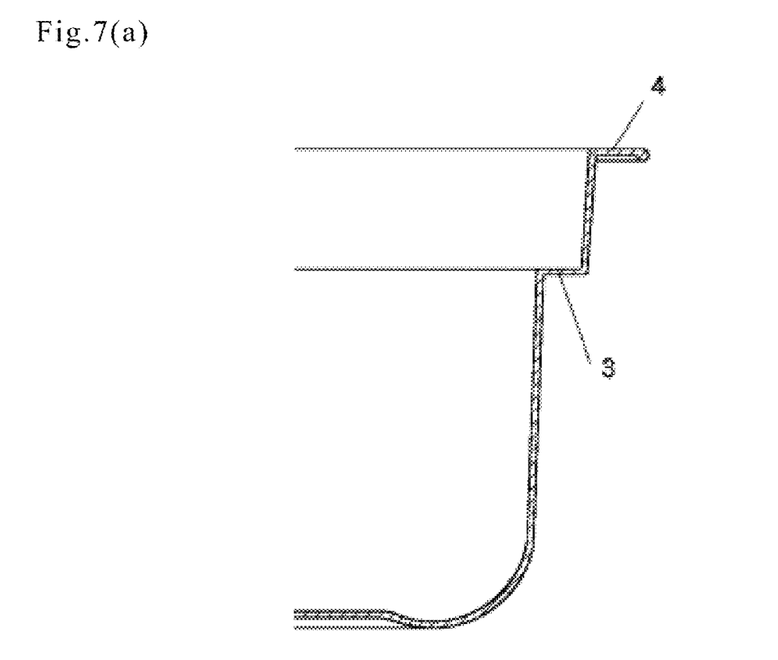
FIG. 7(a) A cross-sectional view of only a main body 10 of the conventional medical container illustrated in FIG. 6 as viewed in the direction of arrows B-B.
Figure 7B:
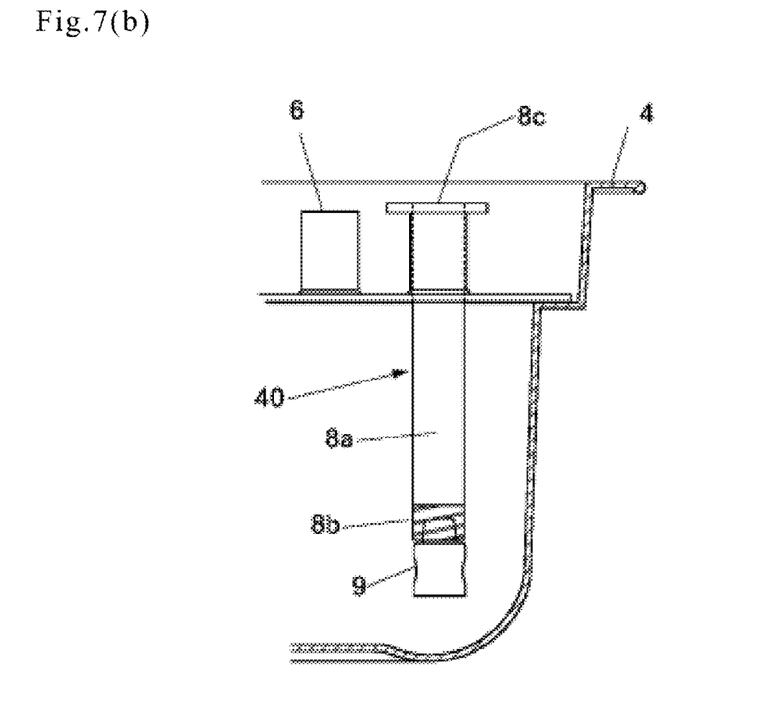
FIG. 7(b) A cross-sectional view, as viewed in the direction of arrows B-B, of a state that the holder 30 with the syringe barrels 40 held thereon in the conventional medical container shown in FIG. 6 has been arranged in the container main body 10.

When such a medical container is employed, the plural syringe barrels 40 are held upright, and moreover, medicament fill ports 8c of the syringe barrels 40 are directed upwards (see FIG. 3). The use of such a medical container, therefore, has such merits as will be described below. As a syringe barrel manufacturer is generally different from a medicament manufacturer, syringe barrels are shipped from the syringe barrel manufacturer and are then transported to the medicament manufacturer. At the medicament manufacturer as the destination of the transportation, filling of a medicament into the syringe barrels transported as described above is performed. In this case, the employment of such a medical container enables the medicament manufacturer to concurrently conduct sterilization treatment to the plural syringe barrels and to store and transport the sterilized plural syringe barrels together. If the plural syringe barrels transported in the medical container from the syringe barrel manufacturer to the medicament manufacturer are equipped on the needle fitting side 8b thereof with nozzle caps 9, respectively, as shown in FIG. 7(b), it is possible to obviate at the medicament manufacturer a step that would otherwise be needed to bring the nozzle caps 9 into engagement with the syringe barrels. When the syringe barrels are delivered in the above-described state, a filling operation can be efficiently conducted by taking the holder 30 together with the plural syringe barrels 40 held thereon out of the container 10 and transporting it, as it is, to a medicament filling machine (not shown). More specifically, the medicament can be filled into the respective syringe barrels at the same time by filling the medicament from plural filling nozzles, which are arranged on the filling machine, into the exposed fill ports 8c of the syringe barrels 40.

It is to be noted that, as medical syringes require to place ultimate priority on safety, each container containing plural syringe barrels placed therein and being to be shipped from a syringe barrel manufacturer needs to be sterilized fully in the state and to be distributed or stored with the sterilized state being maintained. As a method for bringing the interior of a container into a sterilized state, sterilization treatment is conducted by such a method as covering an opening in an upper part of the container with a cover sheet (cover) having low gas permeability, fixedly securing the sheet on the container, and then irradiating electron beams in the state (see Patent Documents 1 and 2). For the container containing the plural syringe barrels placed therein and being to be shipped from the syringe barrel manufacturer, it is desired, as another demand, to prevent the occurrence of rattling of the syringe barrels in the container, said ratting being a potential cause for the formation of scratches or like damages during the transportation. It is also desired that, when the holder 30 is taken out of the container 10 and the medicament is filled into the plural syringe barrels 40 held on the holder 30, the plural syringe barrels 40 are in such a state as permitting precise filling of a medicament into the medicament fill ports 8c of all the syringe barrels 40.

Patent Document 1: JP-A-2004-513707
Patent Document 2: JP-A-2004-513708

DISCLOSURE OF THE INVENTION

Problem to Be Solved by the Invention

However, the conventional method that covers a container with a cover sheet requires to perform heat sealing of a main body of the container with the sheet as a cover, so that cumbersome steps are needed. Further, this method is hardly applicable when the interior of the container is to be subjected to sterilization treatment with gas, although it is suited for sterilization treatment by electron beams. In addition, the method that covers the container with the cover sheet involves a problem that during transportation, syringe barrels rattle and may be scratched or otherwise damaged in some instances. As a method for maintaining a sterilized state of a medical container, the container may be placed in a bag made of a gas impervious film, and the interior of the bag may then be brought into a reduced-pressure state. According to this method, the problem of rattling syringe barrels does not occur. Described specifically, when a container is placed in a bag made of a gas impervious film and the interior of the bag is brought into a reduced-pressure state, the film is pressed in an air-tight form against flange portions of syringe barrels held in the container, and therefore, rattling of the syringe barrels does not take place during transportation. It has, however, been found that, if excessive pressure reduction is conducted to press the film in an air-tight form against the syringe barrels, the excessive pressure reduction may be produce warpage on a holder. When warpage is produced on the holder, the holding direction of syringe barrels may vary in extreme cases, thereby leading to a potential problem that a gripping failure or transport failure may take place at a pick-up device for taking out syringe barrels from the holder or at a transport apparatus or that a filling failure may take place at a filling machine for filling a medicament into syringe barrels.

Therefore, an object of the present invention is to provide a medical container of a construction that can be readily and promptly brought into a sterilized state by various methods such as gas or electron beams, can be readily and promptly brought into a state capable of maintaining the sterilized state, and during transportation, can fixedly secure, without rattling, syringe barrels held upright by holders. Another object of the present invention is to provide a medical container, which can firmly hold, without rattling, plural syringe barrels hooked and held upright at flange portions thereof on cylindrical portions of a holder and the holder is free from producing warpage during the holding to contribute to an improvement in the efficiency of a medicament filling operation.

Means for Solving the Problem

The above-described objects of the present invention can be achieved by the present invention to be described hereinafter. Specifically, the present invention relates to a medical container useful upon transportation of plural syringe barrels, comprising at least a container main body 10 and a holding member 30 arranged inside the container main body 10; wherein the holding member 30 is provided at least with a plurality of cylindrical holding portions 6 for holding syringe barrels; wherein the container main body 10 has at least a peripheral rim 4 arranged on and along an outer periphery of an opening and a shoulder-shaped portion 20 arranged on an inner wall of the container to arrange the holding member 30; and wherein the shoulder-shaped portion 20 has at least three ribs 1 for supporting the holding member 30, and has a structure that enables to arrange via the ribs 1 the holding member 30 in a horizontal position relative to a bottom wall of the container main body 10.

As a preferred embodiment of the present invention, there can be mentioned a medical container including an additional constitution that the shoulder-shaped portion 20 is arranged at a height such that, in a state that the holding member 30 is arranged on the shoulder-shaped portion via the ribs 1 while holding the syringe barrels at the cylindrical holding portions 6, a height of an uppermost end of each syringe barrel from the bottom wall of the container main body 10 is equal or higher compared with a height of an upper wall of the plate-shaped peripheral rim 4 of the container main body 10 from the bottom wall of the container main body. When constructed as described above, a gas impervious film can be pressed in an air-tight form against flange portions of the syringe barrels held in the medical container by simply placing the container in a bag made of the gas impervious film and bringing the interior of the bag into a state lightly reduced in pressure. In this respect, a description will be made subsequently herein. Here, the expression "a height . . . equal . . . compared with a height . . . from the bottom wall" specifically has the following meaning. It means a structure that, when syringe barrels 40 held on the holder 30 are arranged in the container main body 10, the height of the uppermost ends of the syringe barrels 40, specifically flange walls, in which medicament fill ports 8c are formed, from the bottom wall of the container main body 10 is substantially the same as the height of the upper wall of the plate-shaped peripheral rim 4 arranged on and along the outer periphery of the opening of the container main body 10 from the bottom wall of the container main body. In other words, the above expression does not mean that both of the heights are exactly the same, and means that the former height may be slightly lower than the latter height.

Advantageous Effects of the Invention

According to the present invention, there is provided a medical container which, compared with conventional medical containers, makes it possible to readily and promptly bring its interior into a sterilized state by various methods such as gas or electron beams and also to readily and promptly maintain the sterilized state. According to the present invention, there is also provided a medical container capable of readily holding plural syringe barrels, which are held on a holder, in a rattling-free state during transportation without producing warpage on the holder. According to the present invention, there is further provided a medical container of the construction that the above-described excellent effects can be achieved without performing a cumbersome operation such as heat sealing unlike the conventional art.

BEST MODES FOR CARRYING OUT THE INVENTION

Based on preferred embodiments, the present invention will hereinafter be described in detail with reference to drawings. A medical container according to the present invention comprises a container main body 10 and a holder 30 for holding syringes 40, and features a structure that brings about the following state when the holder 30 is arranged in the container main body 10. For the sake of comparison, the structure of a conventional medical container is depicted in FIG. 6, FIG. 7(a) and FIG. 7(b).

Figure 4A:
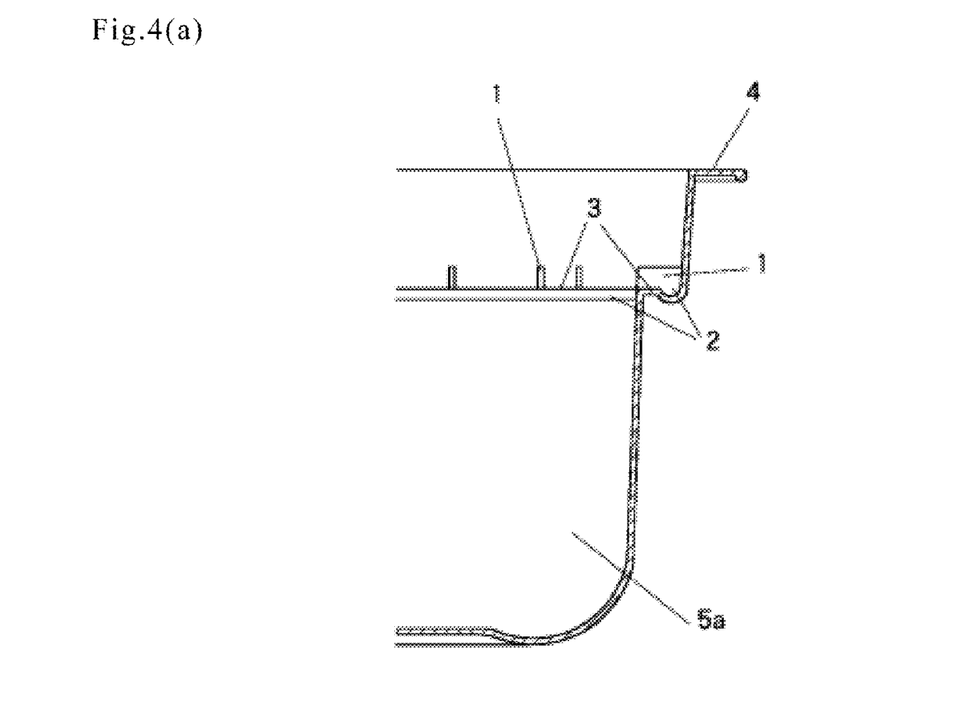
FIG. 4(a) A cross-sectional view of only the container main body 10 shown in FIG. 2(a) as viewed in the direction of arrows A-A.
Figure 4B:
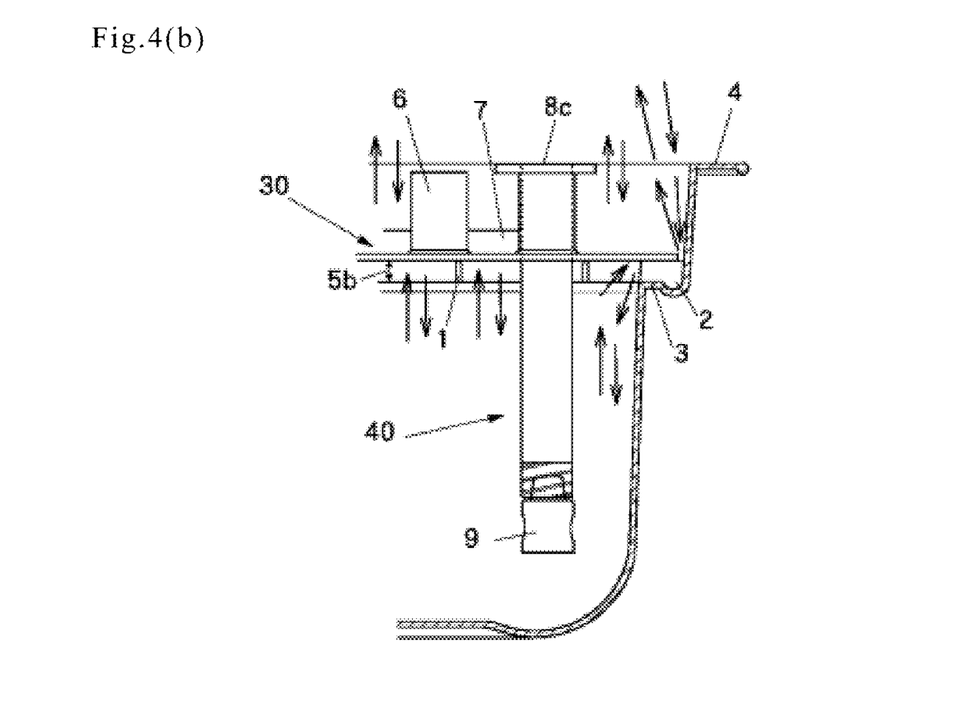
FIG. 4(b) A cross-sectional view of the state that as shown in FIG. 2(b), the holder 30 with the syringe barrels 40 held thereon has been arranged in the container main body 10 as viewed in the direction of arrows A'-A'.

Described firstly, as the holder 30 that constitutes the medical container according to the present invention, a conventionally-known holder can be used. As the general shape of the holder 30, it is in the form of a plate, and it has a structure that the plate is provided with a plurality of cylindrical holding portions 6 to hold syringe barrels. A similar holder can also be used in the present invention. As shown in FIG. 3, the holder 30 is used with the syringe barrels 40—which are provided, for example, at tips thereof with nozzle caps 9—held on the respective holding portions 6. Similar to the conventional medical containers, the holder 30 is arranged on a shoulder-shaped portion 20 which is provided on an upper part of an inner wall of the container main body 10, and is arranged at a predetermined distance from the bottom wall of the container main body 10 and in a horizontal position relative to the bottom wall of the container. As readily appreciated from the foregoing, the holder 30 is a nest to be arranged in the container main body 10, and in this respect too, the medical container according to the present invention has no different features whatsoever from the conventional medical containers. A characteristic feature of the medical container according to the present invention resides in a structure that in the foregoing, the holder 30 is supported by ribs 1 and is arranged via the ribs 1 on the shoulder-shaped portion 20 provided on the container main body 10. Because the medical container according to the present invention has the construction as described above, the holder 30 is not in contact with a shoulder 3, which constitutes the shoulder-shaped portion 20, unlike the conventional containers (see FIG. 7(b)), and a clearance 5b is formed between the holder 30 and the shoulder 3 (see FIG. 4(b)) . As a consequence, the use of the medical container according to the present invention allows to more promptly purge the interior 5a of the container with sterilizing gas and to perform more efficient sterilization treatment as shown in FIG. 4(b) compared with the use of a medical container of the conventional structure upon filling the interior of the container with the gas. A similar advantage is also available when the container is covered with a film having low gas permeability and the internal gas is eliminated.

No particular limitation is imposed on the shape of the container main body 10 of the medical container according to the present invention. It is, however, possible to use a container main body in the form of an upwardly open box which has been used conventionally. As a preferred form of the medical container according to the present invention, the container main body 10 can be in the form of an upwardly open box as in the conventional art, the shoulder-shaped portion 20 composed of four sides continuously extending along an entire periphery of the inner wall of the container main body 10 can be arranged, and the ribs 1 can be formed as many as one or more per side of the shoulder-shaped portion 20. In the present invention, the holder 30 is supported by the ribs 1 that constitute the shoulder-shaped portion 20. It is, therefore, only necessary to permit the arrangement of the holder 30 in the container main body 10 via the ribs 1. As the number of the ribs 1, it is hence sufficient if there are at least three ribs. To more stably arrange the holder 30 in the container main body 10, however, it is preferred to arrange four or more ribs as described above. More preferably, it is possible to construct such that the ribs 1 are arranged at intervals of preferably from 1 to 6 cm or so, more preferably from 2 to 5 cm or so, still more preferably from 2 to 3 cm or so. When constructed so, gas is allowed to flow through a passage defined by each adjacent two ribs 1 to achieve faster movement of the gas so that the interior of the container can be more easily purged with sterilizing gas. For the purpose of maintenance the sterilized state in the container, it can also be practiced to cover the container by a film having low gas permeability and further, to eliminate the internal gas to bring the interior into a reduced pressure state. In this case, the greater the number of the ribs, the more the load to be applied to the individual ribs can be distributed. The arrangement of ribs in a greater number is also preferred from this standpoint. When plural ribs are arranged, the intervals of the ribs themselves may be the same, or may be designed such that the intervals differ depending on the position.

Figure 1:
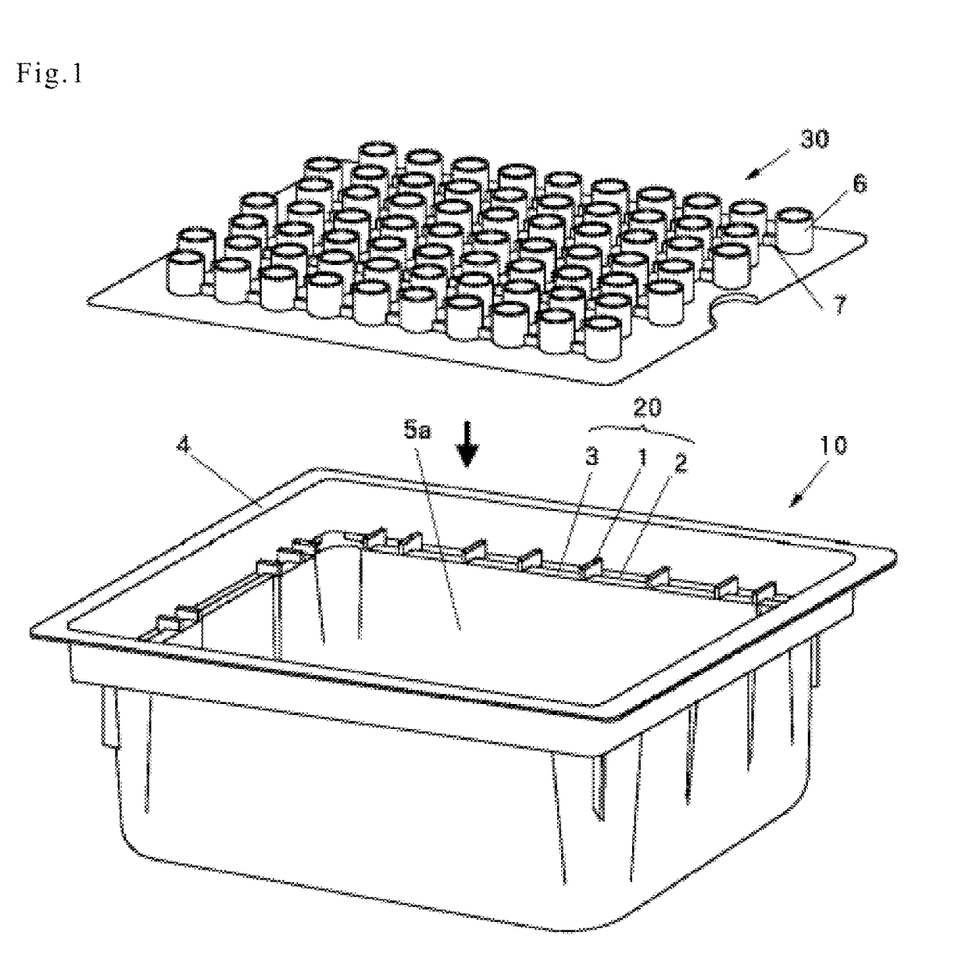
FIG. 1 A perspective view for describing the construction of one example of a medical container according to the present invention.
Figure 2A:
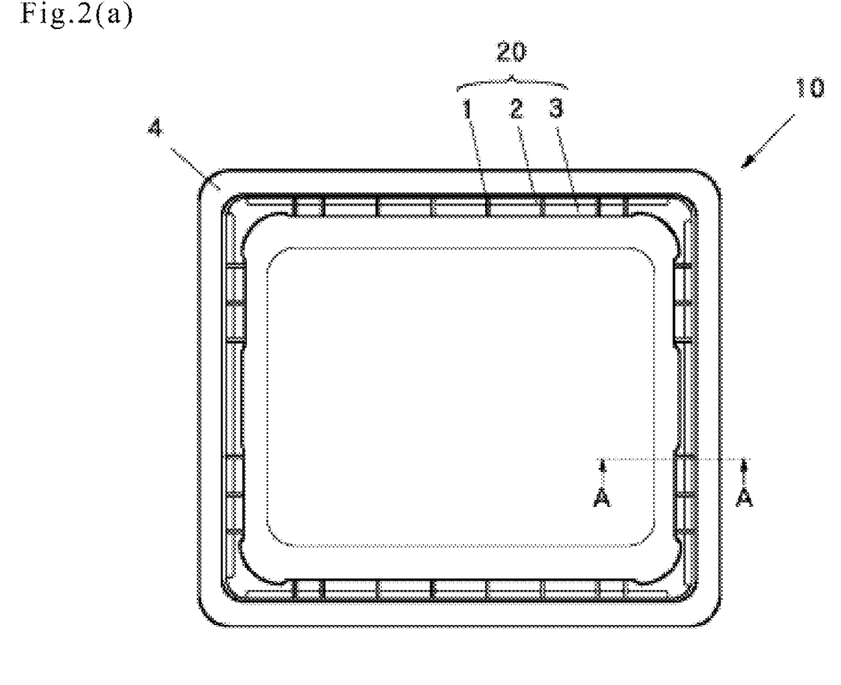
FIG. 2(a) A plan view of a container main body 10 constituting the medical container according to the present invention as illustrated by way of example in FIG. 1.
Figure 2B:
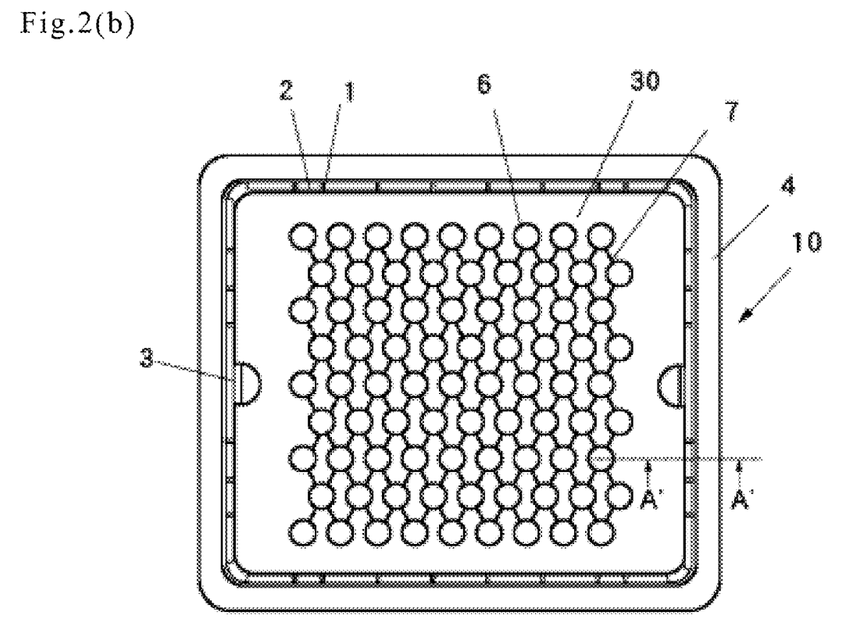
FIG. 2(b) A plan view of a state that a holder 30 constituting the medical container according to the present invention as illustrated by way of example in FIG. 1 has been arranged in the container main body 10.

As a preferred embodiment of the medical container according to the present invention, there can be mentioned one further provided at the shoulder-shaped portion with a recessed groove portion 2 arranged on and along the inner wall of the container. As shown in FIG. 1, FIG. 2(*a*) and FIG. 2(*b*), it is preferred in such a preferred embodiment to form ribs 1 of a desired height over the entire width of the strip-like, shoulder-shaped portion 20 in view of a load to be applied to each rib. No particular limitation is imposed on the thickness of the ribs 1. When the ribs 1 are arranged at intervals of from 2 to 5 cm, for example, the ribs 1 may have a thickness of from 1 to 2 mm or so although the thickness varies depending on the number of the ribs. When constructed so, the ribs 1 can steadily support the holder 30 in a stable state even when plural syringe barrels are held on the holder 30.

Figure 5A:
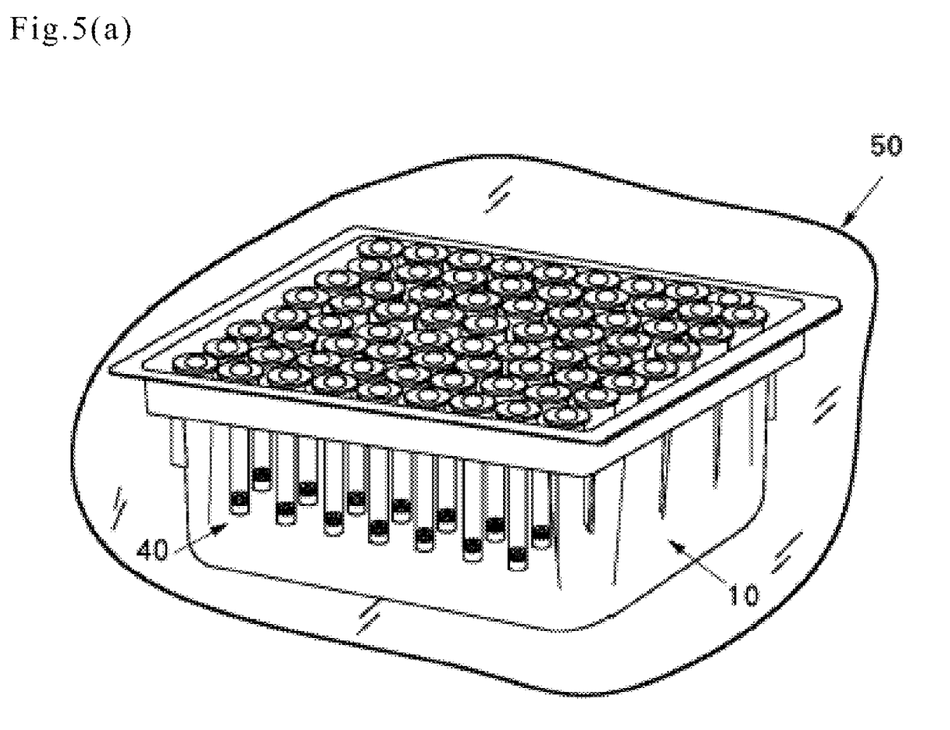
FIG. 5(a) A perspective view illustrating a state that the medical container according to the present invention has been placed in a gas impervious bag.
Figure 5B:
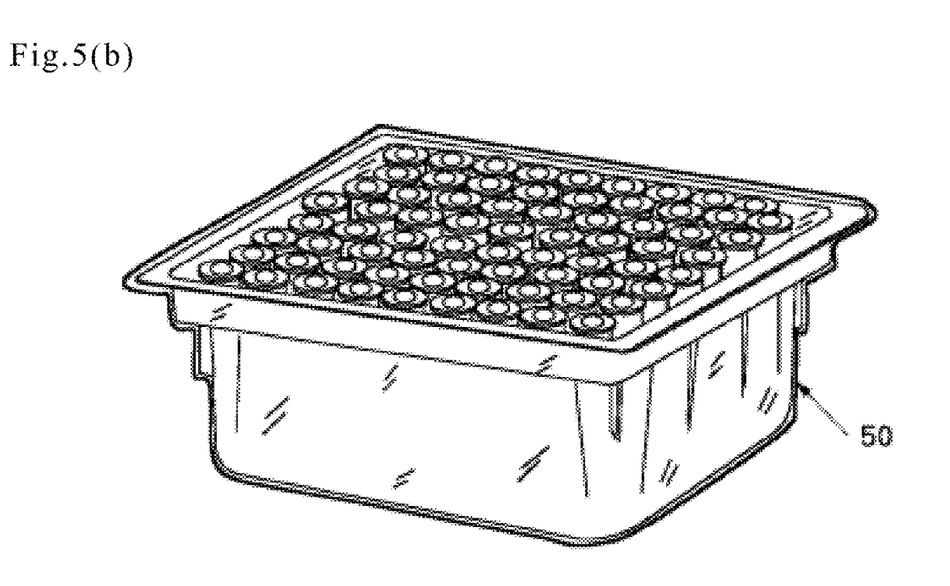
FIG. 5(b) A perspective view depicting a state that the interior of the bag 50 of FIG. 5(a) has been depressurized.

FIG. 5(*a*) and FIG. 5(*b*) are perspective views for explaining the state of use of the medical container according to the present invention. The medical container with the syringe barrels 40 held and stored therein is covered in a bag 50 made of a gas impervious film (see FIG. 5(*a*)), and in this state, the interior of the bag 50 is, for example, filled up with sterilizing gas to conduct sterilization treatment. Subsequently, the interior of the bag 50 is brought into a reduced pressure state to maintain the sterilized state [see FIG. 5(*b*)]. In this manner, the sterilization treatment can be readily and promptly conducted, and moreover, can be readily brought into a state that the sterilized state can be maintained. It is to be noted that, when sterilization treatment is conducted by irradiating electron beams, a bag made of a material which permits transmission of electron beams is used, and subsequent to bringing the interior of the bag 50 into a reduced pressure state, irradiation of electron beams can be performed. When the interior of the bag 50 is brought into the reduced pressure state in the above-described case, the gas impervious film as the material of the bag 50 is brought into close contact with the outer periphery of the medical container as depicted in FIG. 5(*b*). When the interior of the bag 50 is brought into the reduced pressure state, not only the upper wall of a plate-shaped peripheral rim 4 of the container main body 10 but also the flange portions as the uppermost walls of the syringe barrels are brought into close contact with the gas impervious film. As a consequence, the plural syringe barrels 40 held on the cylindrical holding portions 6 of the holder 30 are maintained pressed by the film, and therefore, the syringe barrels 40 do not rattle during transportation.

As an embodiment of the medical container according to the present invention, said embodiment being particularly preferred for the purpose of preventing the syringe barrels 40 from rattling during transportation, it is possible to mention one designed to satisfy the following requirement in addition to the above-described construction. Described specifically, as illustrated in FIG. 4(*b*), it is constituted to arrange the shoulder-shaped portion 20 at a height such that, in a state that the holding member 30 is arranged on the shoulder-shaped portion via the ribs 1 while holding the syringe barrels 40 at the cylindrical holding portions 6, a height of an uppermost end of each syringe barrel from the bottom wall of the container main body is equal or higher compared with a height of an upper wall of the plate-shaped peripheral rim 4 of the container main body 10 from the bottom wall of the container main body 10. The adoption of such an embodiment can bring about a further advantageous effect.

Described specifically, when it is constructed such that as illustrated in FIG. 4(*b*), the upper wall of the plate-shaped peripheral rim 4 of the container main body 10 and the uppermost end of each syringe barrel in the state that the syringe barrel is held on the holder 30 lie on substantially the same plane or the uppermost end of the syringe barrel is higher than the upper wall of the plate-shaped peripheral rim 4 of the container main body 10, the gas impervious film is brought into close contact with the uppermost end of each syringe barrel even in a lightly reduced pressure state when the medical container is placed in the bag made of the gas impervious film and is brought into a reduced pressure state. As a consequence, compared with a case that as depicted in FIG. 7(*b*), a medical container that the uppermost end of each syringe barrel is located at a position lower than the upper wall of the peripheral rim 4 of the container main body 10 is used, each syringe barrel can be fixedly secured with ease in the state that the reduced-pressure state inside the bag is low. In the case of the conventional embodiment illustrated in FIG. 7(*b*), for example, the interior of the bag has to be depressurized to 400 Torr or so in order to bring the film into close contact with the uppermost end of each syringe barrel. In the case of the medical container of the present invention constructed as described above, on the other hand, the film can be brought into close contact with the uppermost end of each syringe barrel when the interior of the bag is brought into a reduced pressure state of 500 Torr or so. According to the medical container of each of the preferred embodiments of the present invention, the syringe barrels can be easily prevented from rattling in the container during transportation as described above.

Compared with the preferred embodiments of the present invention, the embodiment shown in FIG. 7(*b*) requires greater depressurization of the interior of the bag to bring the gas impervious film into close contact with each syringe barrel. As the interior of the bag is progressively depressurized, a higher load is applied onto the holder 30 via the gas impervious film which is maintained in the close contact. There is hence the potential problem that warpage may be produced on the holder 30 in some instance. If warpage is produced on the holder 30, the state of the holding of the plural syringe barrels 40 becomes no longer uniform, and in a worst case, the holding direction of some of the held syringe barrels may vary. This means that, when the plural syringe barrels held on the holder 30 are concurrently filled with a medicament by using a filling machine, the filling of the medicament to all the syringe barrels cannot be performed evenly, leading to a potential problem that a filling failure may take place.

The holder 30 which constitutes the medical container according to the present invention may preferably be in such a form that as depicted in FIG. 1 and FIG. 2(b), the cylindrical holding portions 6 which constitute the holder 30 are adjacently connected to each other by connecting ribs 7. As mentioned above, the holder 30 with the plural syringe barrels 40 held thereon can be taken out of the container, and in the same state, a medicament can be filled into the respective syringe barrels by a medicament filling machine. A substantial load can, therefore, be applied to the holder 30. When designed into the structure that the holding portions 6, which constitute the holder 30, are connected with each other by the connecting ribs 7, the strength of the whole holder 30 can be heightened so that high durability can be imparted to the holder 30.

As also mentioned above, the medical container according to the present invention may preferably be constructed in the embodiment that at the shoulder-shaped portion 20, the recessed groove 2 is arranged along the inner wall of the container. When constructed in this embodiment, the container main body 10 can be provided with heightened strength. Described specifically, the container is free from breakage even when a high load is applied onto the upper wall of the plate-shaped peripheral rim 4 of the container main body 10 upon placing the medical container according to the present invention in the bag 50 made of the gas impervious film and bringing the interior of the bag into a reduced pressure state.

LEGEND

1: Rib
2: Groove
3: Shoulder
4: Peripheral rim
5a: Interior of container
5b: Clearance
6: Holding portion
7: Connecting rib
8a: Barrel portion of syringe barrel
8b: Needle fitting
8c: Fill port of syringe barrel
9: Nozzle cap
10: Main body of container
20: Shoulder-shaped portion
30: Holder
40: Syringe barrel
50: Gas impervious film

The invention claimed is:

1. A medical container useful upon transportation of plural syringe barrels, comprising:
    at least a container main body and a holding member arranged inside said container main body;
    wherein said holding member has a top surface and a bottom surface and is provided at least with a plurality of cylindrical holding portions for holding syringe barrels;
    wherein said container main body has at least a peripheral rim arranged on and along an outer periphery of an opening and a shoulder-shaped portion arranged on an inner wall of said container to arrange said holding member;
    wherein said shoulder-shaped portion has a top surface and a bottom surface and has at least three ribs formed on a top surface of the shoulder shaped portion for supporting said holding member;
    wherein the at least three ribs each has a first side surface and a second side surface, the first and second side surfaces extending toward a top-most portion that is located between the first and second side surfaces, and wherein the top-most portion of each rib extends in a horizontal direction so as to define a horizontal plane; and
    wherein a clearance is formed between the bottom surface of the holding member, the top surface of the shoulder shaped portion and opposing surfaces of at least two adjacent ribs when the holding member is arranged inside of the container.

2. A medical container useful upon transportation of and configured to receive plural syringe barrels, comprising:
    at least a container main body and a holding member arranged inside said container main body;
        wherein said holding member has a top surface and a bottom surface and is provided at least with a plurality of cylindrical holding portions for holding syringe barrels, the syringe barrels each having a top surface which defines an uppermost end of each syringe barrel;
        wherein said container main body has at least a peripheral rim arranged on and along an outer periphery of an opening and a shoulder-shaped portion arranged on an inner wall of said container to arrange said holding member;

wherein said shoulder-shaped portion has a top surface and a bottom surface and has at least three ribs formed on a top surface of the shoulder shaped portion for supporting said holding member;

wherein the at least three ribs each has a first side surface and a second side surface, the first and second side surfaces extending toward a top-most portion that is located between the first and second side surfaces, and wherein the top-most portion of each rib extends in a horizontal direction so as to define a horizontal plane;

wherein a clearance is formed between the bottom surface of the holding member, the top surface of the shoulder shaped portion and opposing surfaces of at least two adjacent ribs when the holding member is arranged inside of the container; and wherein said shoulder-shaped portion is arranged at a height such that, in a state that said holding member is arranged on said shoulder-shaped portion via said ribs while holding said syringe barrels at said cylindrical holding portions, a height of the uppermost end of each syringe barrel from said bottom wall of said container main body is equal or higher compared with a height of an upper wall of said plate-shaped peripheral rim of said container main body from said bottom wall of said container main body.

3. A medical container according to claim 1, wherein said shoulder-shaped portion is further provided with a recessed groove portion arranged on and along said inner wall of said container.

4. A medical container according to claim 1, wherein said container main body is a form of an upwardly-open box, a shoulder-shaped portion composed of four sides continuously extending along an entire periphery of said inner wall of said container main body is arranged, and said ribs are formed as many as at least one per side of said shoulder-shaped portion.

5. A medical container according to claim 1, wherein said cylindrical holding portions are adjacently connected to each other via connecting ribs.

6. A medical container for receiving and transporting syringe barrels, comprising:

a container main body having bottom wall, a plurality of inward facing side walls, an opening, and a shoulder shaped portion integral with the plurality of inward facing side walls, the shoulder shaped portion including at least three rib portions and a shoulder integrally formed therein; and a holding member capable of being arranged inside the container main body, the holding member having a top and bottom surface, opposing peripheral edges and a plurality of cylindrical holding portions for holding syringe barrels, wherein the at least three rib portions each has a first side surface and a second side surface, the first and second side surfaces extending toward a top-most portion that is located between the first and second side surfaces, and wherein the top-most portion of each rib extends in a horizontal direction so as to define a horizontal plane, wherein a clearance is formed between the bottom surface of the holding member, a top surface of the shoulder shaped portion and opposing surfaces of at least two adjacent ribs when the holding member is arranged inside of the container, and wherein the opposing peripheral edges of the holding member are spaced away from adjacent surfaces of the plurality of inward facing side walls so as to define a continuous opening.

\* \* \* \* \*